(12) United States Patent
Thorn et al.

(10) Patent No.: US 8,449,489 B2
(45) Date of Patent: May 28, 2013

(54) METHOD AND MEANS FOR TREATING INFLAMMATORY BOWEL DISEASE

(75) Inventors: Magnus Thorn, Uppsala (SE); Ola Winqvist, Uppsala (SE)

(73) Assignee: ITH Immune Therapy Holdings AB, Stockholm (SE)

( * ) Notice: Subject to any disclaimer, the term of this patent is extended or adjusted under 35 U.S.C. 154(b) by 832 days.

(21) Appl. No.: 12/300,501

(22) PCT Filed: May 14, 2007

(86) PCT No.: PCT/SE2007/000459
§ 371 (c)(1),
(2), (4) Date: Nov. 12, 2008

(87) PCT Pub. No.: WO2007/133147
PCT Pub. Date: Nov. 22, 2007

(65) Prior Publication Data
US 2009/0192434 A1    Jul. 30, 2009

(30) Foreign Application Priority Data
May 12, 2006 (SE) ...................................... 0601075

(51) Int. Cl.
*A61M 37/00* (2006.01)
*A61K 39/395* (2006.01)
(52) U.S. Cl.
USPC ..................................... 604/6.03; 424/178.1
(58) Field of Classification Search
USPC ................... 604/4.01–6.16; 424/178.1–183.1
See application file for complete search history.

(56) References Cited

U.S. PATENT DOCUMENTS

| 6,866,846 B1 | 3/2005 | Heinrich et al. |
| 2004/0052681 A1 * | 3/2004 | Mortensen et al. ............. 422/45 |

FOREIGN PATENT DOCUMENTS

| DE | 10 2005 036 505 A1 | 6/2006 |
| JP | 11-158076 | 6/1999 |
| WO | 0012113 | 3/2000 |
| WO | 0224307 | 3/2002 |
| WO | WO 02/24307 A2 * | 3/2002 |
| WO | WO 2006/125201 A2 | 11/2006 |
| WO | WO 2007/133147 A1 | 11/2007 |
| WO | WO 2008/038785 A1 | 4/2008 |

OTHER PUBLICATIONS

Emmerich, Joerg et al., "Mobilization of Mucosa Lymphocytes by Leukocytapheresis", Gastroenterology, 130, (2006): suppl. 2, Apr. 2006.*
Sandborn, William et al., "Biologic Therapy of Inflammatory Bowel Disease" Gastroenterology 2002, 122, pp. 1592-1608.*

(Continued)

*Primary Examiner* — Philip R Wiest
(74) *Attorney, Agent, or Firm* — Jason M. Pass

(57) ABSTRACT

A method of treating inflammatory bowel disease (IBD) comprises providing an intestinal biopsy sample obtained from inflamed tissue of a patient; mechanically treating the sample to obtain a cell suspension; identifying cell surface markers of activated leukocytes selected from T lymphocytes, neutrophil granulocytes, and eosinophil granulocytes in the suspension; raising antibodies against one of more of the activated cells and immobilizing them on a support; providing a column loaded with the support; diverting a portion of the patient's peripheral blood to make it pass through the column before re-infusing it to the patient to make the activated leukocytes couple with antibodies on the support, thereby eliminating them from the blood stream. Also disclosed are corresponding columns and supports, and their use in the method.

20 Claims, 10 Drawing Sheets

OTHER PUBLICATIONS

Joerg Emmrich et al., "Mobilization of Mucosa Lymphocytes by Leukocytapheresis", Gastroenterology, 130, (2006): suppl. 2, Apr. 2006.

J. Polko et al., National Library of Medicine (NLM), file Medline, Medline accession No. 11968580, "Importance of determination of lymphocytes in intestinal mucosa biopsy specimens using flow cytometry in the evaluation of ulcerative colitis activity", vol. 48, No. 3, Mar. 2002, pp. 197-201.

S.J.H. Van Deventer, "New biological therapies in inflammatory bowel disease", Best Practice & Research Clinical Gastroenterology, vol. 17, No. 1, 2003, pp. 119-130.

J. Korber et al., "A Case of Crohn's Disease with Increased CD8 T-Cell Activation and Remission during Therapy with Intravenous Immunoglobulins" Scandinavian Journal of gastroenterology, No. 33, (1998).

William J. Sandborn et al., "Biologic Therapy of Inflammatory Bowel Disease" Gastroenterology 2002, 122, pp. 1592-1608.

Hiroyuki Hanai et al, "Leukocyte Adsorptive Apheresis for the Treatment of Active Ulcerative Colitis: A Prospective, Uncontrolled, Pilot Study", Clinical Gastroenterology and Hepatology, 2003, 1, pp. 28-35.

International Search Report dated Sep. 5, 2007, from corresponding PCT application.

*Database UniProtKB/Swiss-Prot*, XP-002618217, pp. 1-3, Jul. 15, 1998.

*Thermo Scientific—Instruction Sheet*, Instructions: Pierce Momomeric Avidin Kit—XP-002600558, pp. 1-2, Jan. 1, 2007.

*PRV—Swedish Research*, Swedish Search—Forelaggande Med Begaran Om Oversattning (4 Man), pp. 1-8, Mar. 9, 2009.

Calderon et al., *Current Topics in Membranes*, Overview and History of Chemokines and Their Receptors, vol. /Iss: 55, pp. 1-47, Jan. 1, 2005.

Fox et al., *Current Topics in Membranes*, The Molecular and Cellular Biology of CC Chemokines and Their Receptors, vol. /Iss: 55, pp. 73-102, Jan. 1, 2005.

Niess et al., *Current Topics in Membranes*, Chemokines, Chemokine Receptors, and Disease, vol. /Iss: 55, pp. 1-17, Jan. 1, 2005.

Papadakis, K. *Current Allergy and Asthma Reports*, Chemokines in Inflammatory Bowel Disease, vol. /Iss: 4(1), pp. 83-89, Jan. 1, 2004.

Thierry et al., *Journal for Biomolecular Screening*, Biotinylated Synthetic Chemokines: Their Use for the Development of Nonradioactive Whole-Cell Binding Assays, vol. /Iss: 8 (3), pp. 316-323, Jun. 1, 2003.

Van Deventer, S. J. H., *Best Practice & Research Clinical Gastroenterology*, New Biological Therapies in Inflammatory Bowel Disease, vol. /Iss: 17, pp. 119-130, Jan. 1, 2003.

Wiame, Ilse—PCT Officer, *PCT Search Report*, International Search Report and Written Opinion of Application No. PCT/GB2009/002196, pp. 1-8, Feb. 9, 2011.

Zabel et al., *The Journal of Experimental Medicine*, Human G Protein-coupled Receptor GPR-9-6/CC Chemokine Receptor Is Selectively Expressed on Intestinal Homing T-Lymphocytes, Mucosal Lymphocytes, and Thymocytes and Is Required for Thymus-expressed Chemoking-mediated, vol. /Iss: 190 (9), pp. 1241-1254, Nov. 11, 1999.

Japanese Office Action issued in Appl. No. 2009-509488, pp. 1-6, Jan. 24, 2012.

Engelhardt et al., *European Journal of Immunology*, Therapeutic Targeting of a4-integrins in Chronic Inflammatory Diseases: Tipping the Scales of Risk Towards Benefit, vol. /Iss:35, pp. 2268-2273, Jul. 29, 2005.

Kawamura et al., *Japan Apheresis Academic Society Magazine*, New Method of Leukocytapheresis by the Use of Nonwoven Polyester Fiber Filter for Inflammatory Bowel Disease (abstract only), vol. /Iss:19 (1), pp. 28-33, Feb. 29, 2000.

Wiame, Ilse, *EPO Exam Report*, European Exam Report issued in Application No. 09 785 106.7-1212, pp. 1-5, Apr. 4, 2012.

CN Office Action issued in related Chinese Application No: 200780016903.7, pp. 1-7, Jul. 11, 2012.

Hiraishi et al., *Therapeutic Apheresis and Dialysis*, Studies on the Mechanisms of Leukocyte Adhesion to Cellulose Acetate Beads: An In Vitro Model to Assess the Efficacy of Cellulose Acetate Carrier-based Granulocyte and Monocyte Adsorptive Apheresis, vol. /Iss:7 (3), pp. 334-340, Jun. 24, 2003.

Asahi et al., *Therapeutic Apheresis and Dialysis*, Blood Purification Therapies Using Dextran Sulfate Cellulose Columns Liposorber and Selesorb, vol. /Iss:7 (1), pp. 73-77, Feb. 1, 2003.

*EPO Examination Report*, EPO Examination Report issued in Appl. No. 07748123.2, pp. 1-8, Nov. 28, 2011.

Kanai et al., *Expert Opinion in Biological Therapy*, The Logics of Leukocytapheresis as a Natural Biological Therapy for Inflammatory Bowel Disease (XP009135009), vol. /Iss:6 (5), pp. 453-466, May 1, 2006.

Kelsen et al., *Clinical Experiments in Immunology*, Indium-Labelled Human Gut-Derived T Cells from Healthy Subjects with Strong In vitro Adhesion to MAdCAM-1 Show No Detectable Homing to the Gut In vivo, vol. /Iss:138, pp. 66-74, Oct. 1, 2004.

Kitano et al., *Transfusion Science*, Role of LDL Apheresis in the Managment of Hypercholesterolaemia, vol. /Iss:14, pp. 269-280, Jul. 1, 1993.

Lampinen et al., *Gut*, Eosinophil Granulocytes are Activated During the Remission Phase of Ulcerative Colitis, vol. /Iss:54, pp. 1714-1720, Dec. 1, 2005.

Sandborn, William J., *Inflammatory Bowel Disease*, Preliminary Data on the Use of Apheresis in Inflammatory Bowel Disease, vol. /Iss:12 (Suppl. 1), pp. S15-S21, Jan. 1, 2006.

\* cited by examiner

METHOD AND MEANS FOR TREATING INFLAMMATORY BOWEL DISEASE

FIELD OF THE INVENTION

The invention relates to a method of treating inflammatory bowel disease (IBD), in particular ulcerative colitis and Crohn's disease, and means for use in the treatment.

BACKGROUND OF THE INVENTION

Ulcerative colitis and Crohn's disease are manifestations of Inflammatory Bowel Disease (IBD). Other forms of IBD include lymphocytic colitis and collagenous colitis. Patients with fulminant ulcerative colitis are currently treated with high doses of steroids. Clinical phase-III trials with anti-TNFα are under way. Both drugs are general inhibitors of inflammation. They are effective in about 50% of cases but produce serious adverse effects. Frequently, patients may also have recurrent episodes of fulminant colitis. In patients with fulminant colitis not responding to medical treatment prompt surgical intervention is mandatory. Ulcerative colitis is always restricted to the large intestine (colon). In fulminant colitis the colon is resected and an external ileostoma constructed. After recovery and possibly further medical treatment of rectal stump inflammation either ileorectal anastomosis or reconstructive surgery with a pelvic pouch is performed in most patients to restore intestinal continuity. Both operative procedures entail loose stools about six times daily and disturbances in water- and mineral balances.

Patients with Crohn's disease usually have their inflammation in the most distal part of the small intestine and the first part of the large intestine (ileocaecal region), but the inflammation can be located in any part of the gastrointestinal tract. Medical treatment cannot cure the disease although temporary relief may be provided by anti-inflammatory drugs such as steroids and aza-thioprine. Surgery with resection of stenotic and fistulating bowel segments is indicated in about 50% of patients; half of them will have recurrences and need further surgery. Therefore a method which can specifically turn off the inflammation in IBD and prevent recurrent disease in the individual patient is highly warranted.

WO2005113037 discloses a filter and a method for removing selected materials from a biological fluid sample. The filter comprises an outer housing, inlet, and outlet. A plurality of filter surfaces are provided within the outer housing, and at least one coating is applied to the filter surfaces. The at least one coating comprises at least two binding modules that are in turn selectively bound to one another. One binding module is selectively bound to the filter surfaces and another binding module is configured to bind selectively to the selected materials that are to be removed from the fluid sample. As the fluid sample is allowed to pass through the inlet, outer housing, and outlet, the selected materials are selectively bound to the filter surfaces via the coating. The fluid sample is a blood sample. One selected fluid component is a blood component chosen from, i.a., leukocytes, granulocytes, and lymphocytes.

Filter media and apparatus for separation of leukocytes from blood are disclosed in, i.a.: JP2003265596; U.S. Pat. No. 5,885,457; JP04187206; U.S. Pat. No. 4,936,993; JP03000074; JP02167071; JP02009823; JP10057477.

OBJECTS OF THE INVENTION

It is an object of the invention to provide a method for treating IBD, in particular ulcerative colitis and Crohn's disease.

It is another object of the invention to provide means for use in the method.

Further objects of the invention will become evident from the following short description of the invention, of preferred embodiments thereof illustrated in a drawing, and the appended claims.

SUMMARY OF THE INVENTION

In the inflammatory process of IBD T-cells interplay with leukocytes. Noxious agents are released from leukocytes upon stimulation by certain cofactors. These noxious agents damage the intestinal cells. By flow cytometry of material obtained from intestinal biopsies from patients with active IBD we identified leukocyte cell surface markers of activated T lymphocytes and of activated neutrophil and eosinophil granulocytes, cells that are enriched in the inflammatory site, but also present in circulating peripheral blood.

The present invention is based on the hypothesis that these activated cells are responsible for the initiation and maintenance of inflammation in IBD, and that their removal from circulation might reduce and even eliminate such inflammation. The concept comprises the insight that the inflammatory status of each patient is unique in terms of the degree of leukocyte activation and of the kind and relative proportions of invading T cells, parameters that vary from patient to patient and with the severity of the disease, and are influenced by medications administered to the patient. The present invention does not take recourse to the use of unspecific leukocyte adsorbents known in the art, such as cotton and other polymer fibers. In the context of the invention IBD comprises primarily Crohn's disease and ulcerative colitis but also collagenous colitis characterized by watery diarrhoeas, normal endoscopy but histopathological accumulation of collagen in the intestinal submucosa, and lymphocytic colitis characterized by the presence of large amounts of lymphocytes in the intestinal mucosa accompanied by diarrhoea.

According to the invention a patient with IBD is subjected to colonoscopy. One or several biopsies of diseased intestinal tissue are taken. From the single or combined biopsy material a single cell suspension is prepared. The presence of T lymphocytes, B lymphocytes, neutrophil granulocytes and eosinophil granulocytes in the single cell suspension is determined by flow cytometry using antibodies against CD4, CD8, CD3, CD15, CD19. In addition the activation state of the mucosa invading immune cells is investigated by using antibodies against activation markers such as CD69, CD62 L, CD25, CD27, HLA-DR, CD44 and CD66b. In principle, the inflammatory status of each individual patient is unique in terms of degree of activation and type of cell invasion, and parameters that vary with the severity of the disease and upon given medications. Based on the result of this investigation a leukapheresis column is used for the targeted elimination of the dominant inflammatory causing cell population. For eliminating activated T and B lymphocytes antibodies recognizing the activation marker CD69 coupled to a solid support are used. For eliminating activated neutrophil granulocytes antibodies against the gut homing molecule or against CD66b are used; a column loaded with a support on which an integrin α4β7 antibody is immobilized will eliminate leukocytes of this kind. Thus blood cells in the peripheral circulation activated in lymph nodes draining the inflammatory intestinal site en-route to the intestinal mucosa to provide additional local inflammation will be eliminated by such antibody based leukapheresis of peripheral blood. This will dampen or even inhibit additional recruitment of gut autoreactive T cells.

According to the present invention is disclosed a leukapheresis column loaded with a suitable solid support of a large surface to volume ratio, the surface of which carries antibodies capable of binding activated leukocytes circulating in peripheral blood, the activated leukocytes being selected from T lymphocytes, neutrophil granulocytes, and eosinophil granulocytes. Passing peripheral blood from a patient suffering from IBD inflammation through the column will make the activated leukocytes couple with the antibodies and thus eliminate them from the circulation. By homeostatic mechanisms the depletion of activated leukocytes in circulating peripheral blood results in a decreasing number of activated leukocytes trafficking to the intestine and thus in a reduction of the number of activated leukocytes in the intestine. In this application, the term "antibody" comprises antibodies, in particular monoclonal antibodies, and fragments or modifications thereof retaining antigen/antibody binding capability of the corresponding antibody, including recombinant altered antibodies and antigen binding fragments thereof.

This type of "tailored" leukapheresis is capable of sorting out activated leukocytes specifically activated towards the intestinal mucosal cells, thus eliminating an important factor in the inflammatory process and reversing fulminant colitis. In patients with Crohn's disease the same principle applies but the leukocytes; in this case the leukocytes are activated towards antigen(s) located deeper in the intestinal wall. By identifying the antigens causing the inflammation it is possible to select antigens for presenting them in a state immobilized on a solid support to the leukocytes passing through the column, and bind activated leukocytes in this manner.

Based on the intestinal type and degree of inflammatory activation the leukapheresis column is used for the targeted elimination of the dominating inflammation causing cell population. The depletion of activated T lymphocytes in peripheral blood is particularly preferred.

Elimination of activated T lymphocytes from the peripheral blood of an IBD patient by contacting them with antibodies against CD69 or integrin α4β7 antibody is preferred; these antibodies may used alone or in combination. The activated neutrophil granulocytes and eosinophil granulocytes can be eliminated in a corresponding manner by contacting them with antibodies against CD66b and CD9, respectively.

According to the present invention such activated neutrophil granulocytes and eosinophil granulocytes can be also identified in the peripheral blood of an IBD patient.

According to a first preferred aspect of the invention the elimination of activated T leukocytes and/or activated neutrophil granulocytes and/or activated eosinophil granulocytes is achieved by using column comprising more two or more kinds of antibody on the solid support. Preferably a separate support is used for each antibody.

According to a second preferred aspect of the invention the separate supports, each with a different antibody or different antibodies, are disposed in a corresponding number of separate columns. It is preferred for the columns to be coupled in line.

According to a third preferred aspect of the invention several biopsies obtained from a patient with IBD by colonoscopy are combined, mechanically treated to form a single cell suspension, and analyzed by flow cytometry to identify the presence of activated leukocytes selected from T lymphocytes, neutrophil granulocytes, and eosinophil granulocytes, optionally activated B lymphocytes, by exposing them for specific antibodies, in particular antibodies against CD4, CD8, CD3, CD 15, and CD19.

According to a fourth preferred aspect of the invention the activation state of the mucosa invading immune cells obtained from a patient with IBD by colonoscopy is determined by exposing the invading immune cells for antibodies against activation markers such as CD69, CD62 L, CD25, CD27, HLA-DR, CD44 and CD66b.

T lymphocytes prone to migrate into the mucosa of the intestinal wall express the α4β7 integrin receptor that binds to MAdCAM-1 (Mucosal Addressin Cell Adhesion Molecule-1) expressed on the endothelium. According to the present invention such invading T cells can be removed from peripheral circulation by leukapheresis using a column comprising a support on which an antibody to the α4β7 integrin receptor is immobilized.

Thus, a patient with IBD where biopsies investigated by flow cytometry indicate active inflammation can be subjected to antibody based leukapheresis designed to eliminate specific cell populations responsible for the local intestinal inflammation. An intravenous access is introduced in for example antecubital veins coupled to heparinized tubings connecting to a peristaltic pump pumping approximately 30 ml blood per minute. The blood passes through the designed antibody leukapheresis column and the tubing is re-introduced in for example the contralateral antecubital vein. For instance, the patient is subjected to 60 minutes of leukapheresis which will eliminate activated cells from approximately half or little less than half of the blood volume (60×20 ml=1800 ml). Independent of the blood volume eliminated in one leukapheresis the treatment is repeated for 3-5 times within 1 to 3 weeks in order to remove newly appearing blood borne intestinally activated immune cells. The outcome can then be followed by additional investigation of single cells from intestinal biopsies by flow cytometry as outlined above.

According to a particularly preferred aspect of the invention is disclosed a method of treating inflammatory bowel disease (IBD) comprising: (a) providing an intestinal biopsy sample obtained from inflamed tissue of a patient; (b) mechanically treating the sample to obtain a cell suspension; (c) identifying cell surface markers of activated leukocytes selected from T lymphocytes, neutrophil granulocytes, and eosinophil granulocytes in the suspension; (d) raising antibodies against the activated leukocytes; (e) immobilizing the antibodies against the activated leukocytes on a common support or on separate supports; (f) providing a column loaded with the support(s); (g) diverting a portion of the patient's peripheral blood to make it pass through the column before re-infusing it to the patient to make said activated leukocytes couple with the antibodies on the support(s), thereby eliminating them from the blood stream. It is preferred that the supports carrying antibodies against activated T leukocytes and against activated neutrophil granulocytes and/or activated eosinophil granulocytes are provided in separate columns, which may be coupled in line or in parallel. It is also preferred for the method to take recourse to a single column loaded with separate supports on which antibodies against two or more of activated T lymphocytes, activated neutrophil granulocytes, and activated eosinophil granulocytes, optionally activated B lymphocytes, respectively, are immobilized. Preferably the column of the invention has an empty volume of from 20 to 100 ml, in particular from 30 to 50 ml but other, larger volume such as up to 500 ml are also feasible. When columns of a larger volume are used it is important to empty them of blood at the end of treatment to keep blood loss at a minimum. This can be done by flushing them with, for instance, saline until the flushing medium has displaced most of or essentially all blood in the column. Surfaces of the column and the tubing coming into contact with blood should be of a kind so as to prevent coagulation; it is therefore preferred to use columns and tubing with heparinised surfaces. Methods for providing or modifying surfaces that do not activate the coagulation system are well known in the art. so as to Normally, one third to two thirds of the patient's blood volume, preferably about half of its blood volume or slightly less, is made to pass the column in a single treatment. Usually a single treatment will not suffice to obtain remission or long-term freedom or substantial suppression of symptoms. Therefore the treatment is preferably repeated from two or three to five times and more within from one to three weeks from the initial treatment. The intestinal biopsy sample is one of several such samples obtained from the patient and wherein the samples are combined prior to mechanical treatment to provide a cell suspension. Particularly useful in the method of the invention are antibodies against CD69 or integrin α4β7 antibody in respect of activated T lymphocytes in the peripheral circulation, which antibodies are also preferred for immobilization of the support of the invention. The presence of activated T lymphocytes in the intestinal mucosa is advantageously detected by exposing the cell suspension or cells isolated from the suspension to specific antibodies against one or more of the activation markers CD69, CD62 L, CD25, CD27, HLA-DR, CD44, CD66b.

"Raising antibodies" includes the procurement of such antibodies from commercial or other sources.

The invention will now be described in more detail by referring to preferred embodiments thereof illustrated in a drawing.

SHORT DESCRIPTION OF THE FIGURES

DESCRIPTION OF PREFERRED EMBODIMENTS

Materials and methods

Figure 1:
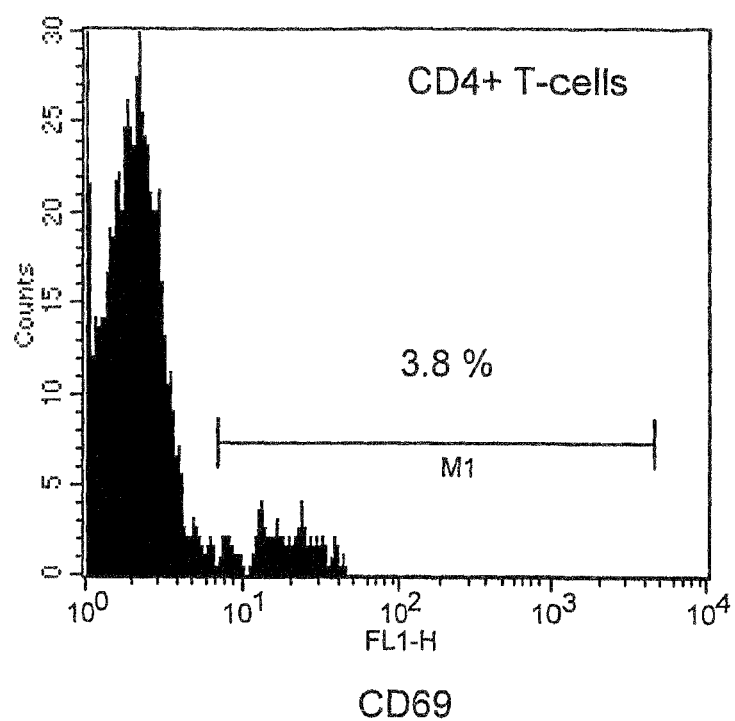
FIGS. 1-4 show the expression of activity markers on CD4+ T cells and neutrophil granulocytes from peripheral blood and intestinal mucosa.

Collection and preparation of samples. During colonoscopy of an IBD patient with fulminant ulcerative colitis biopsy samples were collected, immediately transferred into tubes filled with physiological saline, and further processed within one hour. Single-cell suspensions of biopsy cells were obtained using a loosely fit glass homogeniser. The cells were then washed twice with a buffer for fluorescence activated cell sorting (FACS) containing 0.05% $NaN_3$, 0.1% bovine serum albumin (BSA) and 0.4% trisodium citrate dihydrate in PBS.

Heparinised peripheral blood from the same individual was haemolysed with a 0.83% by weight aqueous ammonium chloride and washed twice in the FACS buffer to obtain a suspension of leukocytes.

The cell suspensions were separately incubated with fluorochrome-conjugated monoclonal antibodies for 30 min at room temperature in the dark. After a final wash, the cells were suspended in 500 µl of the FACS buffer and analysed. Antibodies. Mouse-anti-human mAbs conjugated to fluorescein isothiocyanate (FITC), phycoerythrin (PE), or peridinin chlorophyll protein (PerCP) was used for all antigens (CD4, CD69, CD66b). Isotype-matched control labelling was also performed, using fluorochrome-conjugated mouse anti-human IgM κ and IgG2bκ as controls for non-specific staining. All antibodies used for flow cytometry were purchased from Becton Dickinson (BD) Biosciences/Pharmingen, San Diego, USA. Anti FITC-conjugated MicroBeads (nano-sized supramagnetic particles coupled with specific antibodies) were purchased from Miltenyi Biotech, GmbH, Germany.

Flow cytometry assay. The flow cytometry assay was performed on a two laser FACS Calibur cytometer (BD Immunocytometry systems, San Jose, Calif., USA). Ten thousand cells were counted and analysed in each sample. For data analysis, Cell Quest Pro software from Becton Dickinson was used.

Leukapheresis column. An intravenous access in form of a first cannula 1 is introduced in a antecubital vein 8. The first cannula 1 is coupled to a first heparinized tubing 2 on which a peristaltic pump 3 works, pumping approximately 30 ml blood per minute. At its other end the first heparinized tubing 2 is connected to one end of a leukapheresis column 4 having a volume of 50 ml filled with a granular solid support 5 such as Sepharose® on which an antibody raised against activated T leukocytes harvested from a patient is immobilized. The solid support 5 with the immobilized antibody is held in place by first and second filter bodies 10, 11. The other end of the leukapheresis column 4 is connected to a second heparinised tubing 6 which is coupled to a second cannula 7 at its other end. The second cannula 7 is introduced in the contralateral antecubital vein 9. The venous blood made to flow from the antecubital vein 8 to the contralateral antecubital vein 9 thus is made to pass through the column 4 where activated T lymphocytes couple with the antibody on the support 5 and are so retained in the column. A leukapheresis session is typically one of 60 minutes, which will eliminate activated cells from approximately half or little less than half of the blood volume (depending on the body weight of the person; 60×20 ml=1800 ml). The treatment is repeated, for instance, for 3-5 times within 1 to 3 weeks remove newly appearing blood borne intestinally activated immune cells. The outcome can then be followed by additional investigation of single cells from intestinal biopsies by flow cytometry as described above. In a corresponding manner apheresis of activated neutrophils and/or activated eosinophils is accomplished. Further methods for antibody attachment to solid supports in affinity chromatography useful in the invention are described in Nisevitch M and Firer, M A, J Biochem Biophys Methods 49 (2001) 467-480, which is incorporated in this application by reference.

EXAMPLE 1

MACS separation. Two mL of heparinised peripheral blood from a healthy donor was stimulated with SEB (4 µg/mL) and anti-CD28 monoclonal antibody (10 µg/mL) for 2 hours in 37° C. to obtain activated T cells and neutrophil granulocytes. In order to get a mixed population of activated and resting cells, 2 mL of non-stimulated blood was subsequently added. Leukocytes were fixed, and erythrocytes were removed by hypotonic lysis. The leukocytes were washed and incubated with FITC-conjugated anti CD69 or CD66b. After 10 minutes of incubation in 4° C. in the dark, the cells were washed and incubated for another 15 minutes with anti-FITC microbeads. The cells were separated on a MACS column; both the negative and the positive fractions were collected in different tubes. Finally, the cells were washed and analysed by FACS.

EXAMPLE 2

Figure 2:
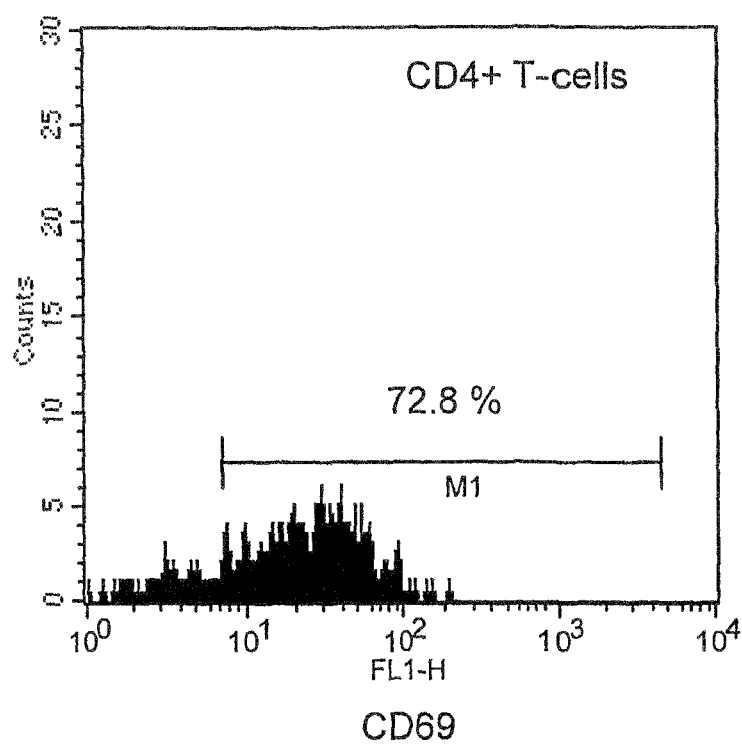

IBD patients have activated CD4+ T cells in peripheral blood and in the intestine. We investigated single cell suspensions from blood and intestinal colon biopsies from 10 patients with Mb Crohn and 12 patients with ulcerative colitis. Patients with IBD display CD4+ T cells in peripheral blood with an activated phenotype, since T helper cells expressing the very early activation marker were found (FIG. 1). In colon biopsies from IBD patients the majority of the CD4+ T cells express the CD69 activation marker as a sign of inflammatory T cell response accumulated in the intestinal wall of the colon responsible for the autoimmune destruction of the colon (FIG. 2). The activated T cells found in peripheral blood are likely T cells that have been activated in an intestinal lymph node draining the inflammatory colon segment, and these cells are on route to the inflammation, a population of cells that should be eliminated.

EXAMPLE 3

Figure 3:
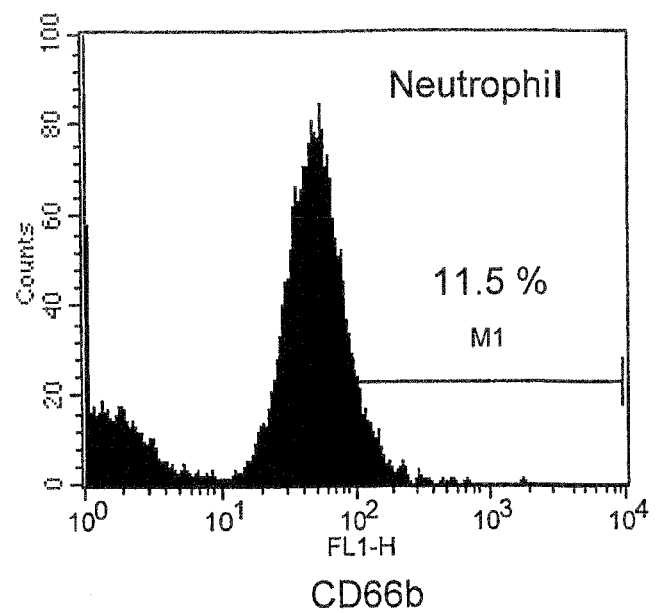

IBD patients have activated neutrophil granulocytes in peripheral blood and in the intestine. Neutrophil granulocytes are a part of the innate immune system and take part in the activation and maintenance of the local inflammation. In peripheral blood from patients with IBD the majority of neutrophil granulocytes express low amounts of CD66b, however a fraction of the neutrophil granulocytes express high amounts of CD66b indicating an activated phenotype (FIG. 3). A substantial portion of the neutrophil granulocytes from colon biopsies from patients with active IBD are CD66bHi (FIG. 4), demonstrating an activation of the innate immune system likely involved in triggering the intestinal inflammation.

EXAMPLE 4

Activated CD4+ T lymphocytes can be eliminated from peripheral blood. Elimination of activated T lymphocytes expressing the CD69 activation marker from peripheral blood (FIG. 5), cells that are en route to the inflamed colon mucosa, can be achieved by using specific antibodies and a column. An aqueous suspension of T lymphocytes labelled with the activation marker CD69 was made to pass through an column loaded with an anti-FITC magnetic bead conjugated secondary antibody. The non-activated T lymphocytes where successfully separated and enriched in the column eluate, showing that the majority of CD69+ cells can be eliminated from peripheral blood (FIG. 6).

EXAMPLE 5

Elimination of activated neutrophil granulocytes from peripheral blood. Activated neutrophil granulocytes identified by their expression of high levels of the cell surface marker CD66b (FIG. 7) were incubated with an anti-FITC magnetic bead conjugated secondary antibody, and subjected to column purification. The majority of the activated neutrophils expressing intermediate to high amounts of the CD66b activation marker were entrapped in the column and thus eliminated from peripheral blood (FIG. 8).

EXAMPLE 6

Exemplary treatment of a patient with IBD. A patient with IBD is subjected to colonoscopy. Several biopsies are taken. A single cell suspension prepared from the combined biopsies. Activated leukocytes, that is, T lymphocytes, B lymphocytes, neutrophil granulocytes and eosinophil granulocytes, in the single cell suspension are identified by flow cytometry using antibodies against, for instance, CD4, CD8, CD3, CD15, CD19. In addition the activation state of the mucosa invading immune cells is determined by using antibodies against activation markers, such as, for instance, CD69, CD62 L, CD25, CD27, HLA-DR, CD44 and CD66b.

A leukapheresis column comprising antibodies against the leukocytes and the mucosa invading immune cells found to be activated is prepared. The volume of the column can be varied within wide limits but for reasons of economy and keeping blood loss at a minimum a volume of approximately 30-50 ml is preferred. The antibodies are immobilized on a suitable support, such as Sepharose®, by any technique for covalently coupling antibodies to a solid support. For instance, antibodies against the activation marker CD69 for eliminating activated T cells and antibodies against the gut homing or against CD66b for eliminating activated neutrophil granulocytes or against the antibody against CD9 for eliminating activated eosinophil granulocytes are used in a particular patient. The column can be provided preloaded with a support on which one or several antibodies are immobilized, or it is individually prepared, such as by a non-covalent immobilization strategy using, for example, a protein A or streptavidin containing support that will bind the Fc domain of the antibody or a biotenylated antibody, respectively. The ready made or individually prepared leukapheresis column is coupled to the peripheral circulation of the patient similar in the manner of an artificial kidney for a time period sufficient to let several blood volumes, preferably from about three to about five blood volumes, pass through it.

EXAMPLE 7

Leukapheresis columns for trapping a specific cell population or a combination of specific cell populations. A column comprising a support loaded with an integrin α4β7 antibody eliminates T cells expressing the gut homing molecule (FIG. 9), thus peripheral blood cells activated in lymph nodes draining the inflammatory intestinal site en-route to the intestinal mucosa causing additional local inflammation will be eliminated in the antibody based leukapheresis procedure. Loading the column with a support carrying an antibody against CD69 will eliminate activated T and B lymphocytes from the blood stream, thus inhibiting additional recruitment of gut auto-reactive T cells. In a similar manner a column loaded with a support carrying an antibody against CD66b will eliminate activated neutrophil granulocytes; for the corresponding elimination of acitvieted eosinophil granulocytes the antibody CD9 is preferred. These supports can be used one-by-one or in combination, such as in parallel or consecutively coupled columns each containing one kind of support or a single column containing several kinds of support such as, for instance, one carrying CD69 and another carrying CD66b. To optimize T cell elimination in a column of given size and solid support the density of antibody on the support surface, antibody affinity, the flow rate of blood passing through the column, etc., can be varied.

Thus, a patient with IBD where biopsies investigated by flow cytometry indicate active inflammation, is subjected to antibody based leukapheresis designed to eliminate specific cell populations responsible for the local intestinal inflammation. An intravenous access is introduced in, for instance, antecubital veins coupled to heparinized tubings affected by a peristaltic pump pumping approximately 30 ml blood per minute. The blood is made to pass through the leukapheresis column of the invention, and the tubing is re-introduced in, for instance, the contralateral antecubital vein. The patient is subjected to 60 minutes of leukapheresis which will eliminate activated cells from approximately half the blood volume (60×20 ml=1800 ml). The treatment is repeated for 3-5 times within 1 to 3 weeks in order to remove newly appearing blood borne intestinally activated immune cells. The outcome can then be followed by additional investigation of single cells from intestinal biopsies by flow cytometry as outlined above.

LEGENDS TO FIGURES

FIG. 1 The expression of the activity marker CD69 is relatively low on peripheral blood CD4+ T lymphocytes (expressed by 3.8% of the CD4+ T cells, with mean fluorescence intensity (MFI) 20.0).

FIG. 2 CD4+ T lymphocytes from the colonic mucosa have an increased expression of CD69 (72.8%, MFI 33.5).

FIG. 3 Most of the peripheral blood neutrophil granulocytes express low amounts of CD66b; but 11.5% have an increased expression indicating cell activation. The MFI of the cells in gate M1 is 104.3.

Figure 4:
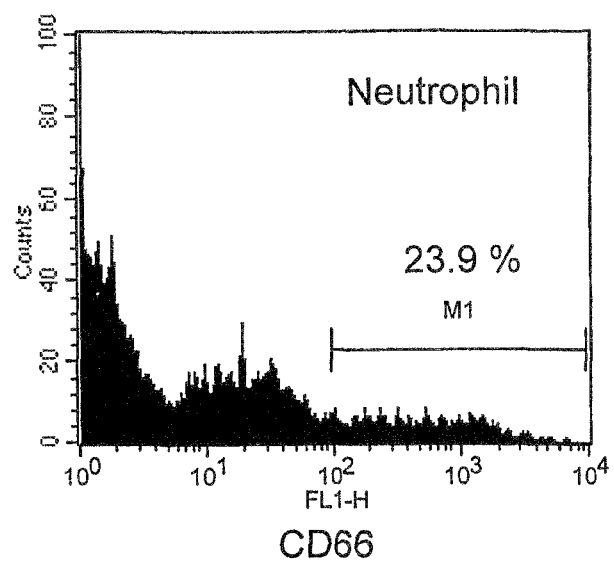

FIG. 4 Neutrophil granulocytes from colonic mucosa have higher MFI of CD66b (629.7 in the gate M1) and an increased proportion of activated neutrophil granulocytes.

Figure 5:
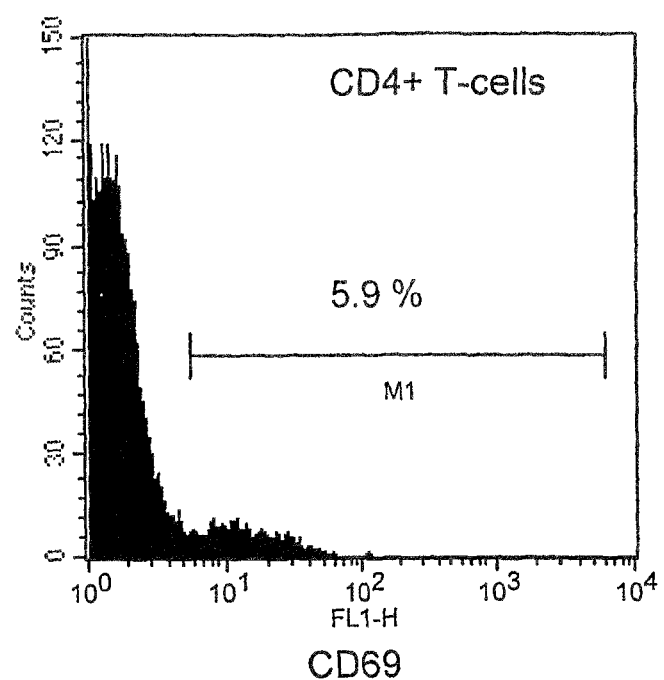
FIGS. 5-9 show the effects of separation of activated peripheral blood CD4+ T cells and neutrophil granulocytes on MACS (Magnetically Activated Cell Sorting) columns.
Figure 6:
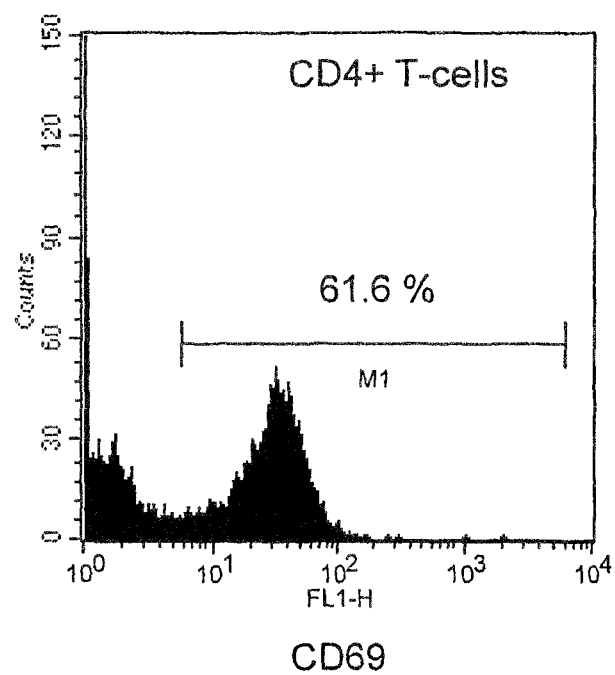

FIG. 5 CD4+ T lymphocytes before separation of CD69-positive cells: 5.9% of the cells express CD69.

FIG. 6 CD4+ T lymphocytes after separation of CD69-positive cells. The positive fraction consists of 61.6% CD69-positive CD4+ T cells.

Figure 7:
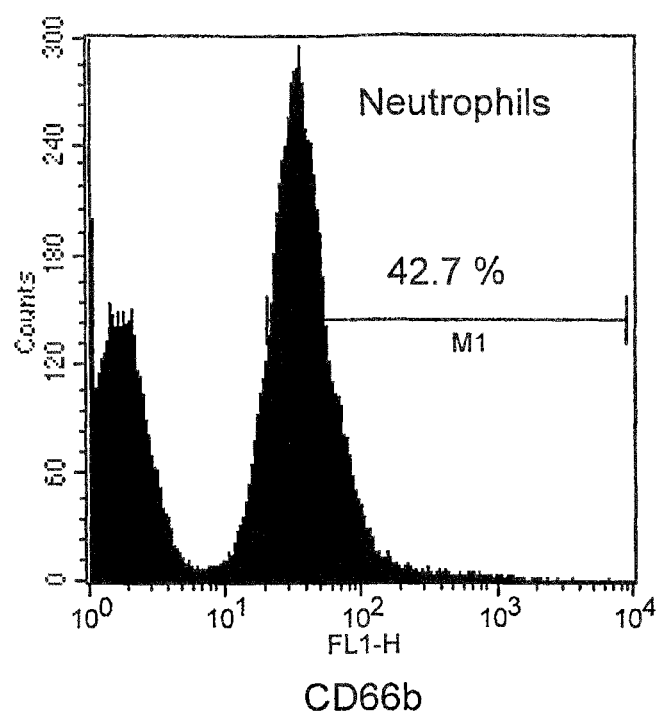
Figure 8:
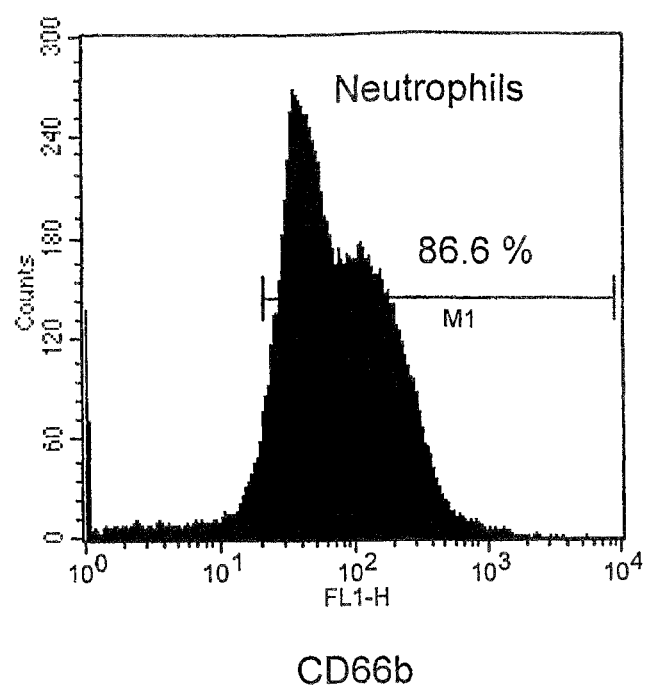

FIG. 7 Neutrophil granulocytes before separation of CD66b-positive cells: 42.7% of the cells have intermediate to high expression of CD66b.

FIG. 8 Neutrophil granulocytes after separation of CD66b-positive cells: 86.6% of the neutrophils in the positive fraction have intermediate to high expression of CD66b.

Figure 9:
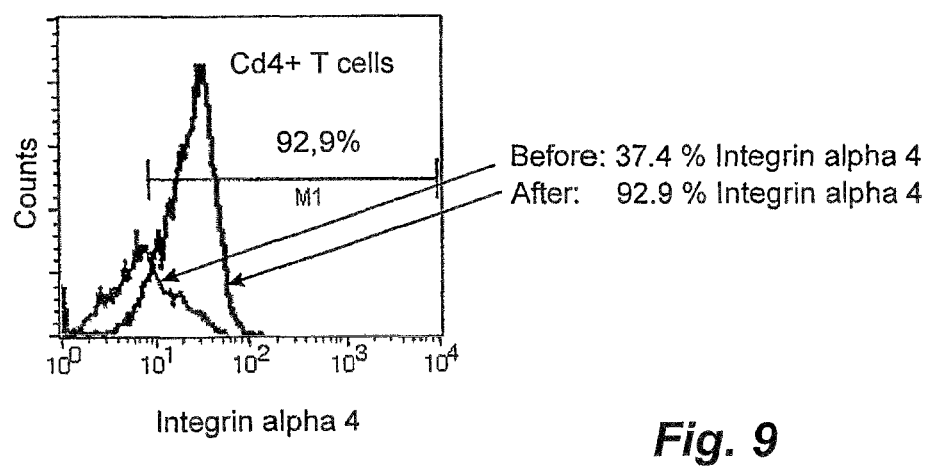
Figure 10:
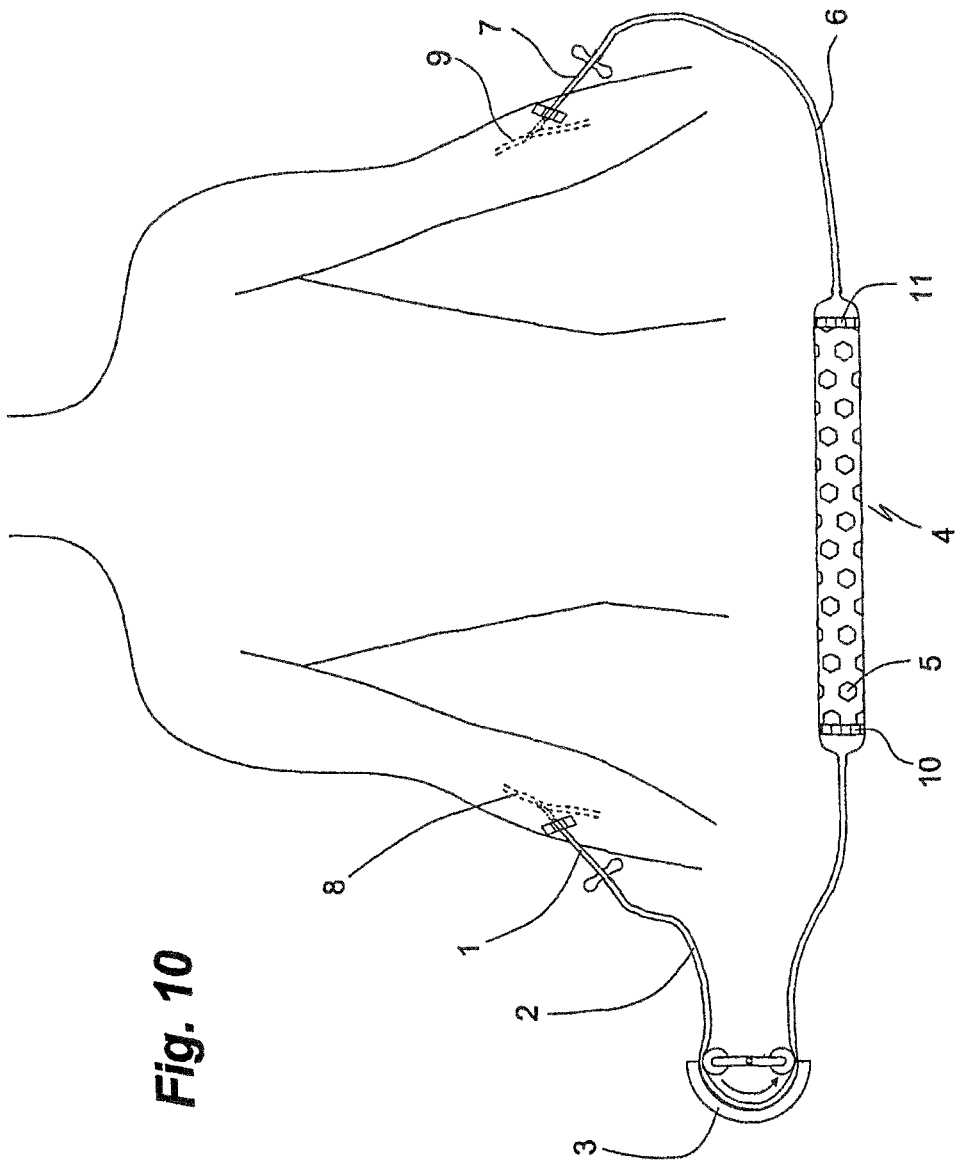
FIG. 10 shows a column of the invention coupled with the circulation of a patient.

FIG. 9 CD4+ T lymphocytes before and after separation of $\alpha 4\beta 7$ integrin positive cells: 37.4% of cells have intermediate to high expression of $\alpha 4\beta 7$ integrin before MACS, and 92.9% after MACS.

The invention claimed is:

1. A tailored leukapheresis column for treating a subject with inflammatory bowel disease (IBD), comprising:
   a column comprising immobilized antibodies that have been selected based on the subject's unique inflammatory response and that are directed against cell surface markers of activated leukocytes selected from the group consisting of T lymphocytes, neutrophil granulocytes, and eosinophil granulocytes,
   wherein the cell surface markers are identified from activated leukocytes obtained from a biopsy sample from inflamed intestinal tissue of the subject with IBD.

2. The column of claim 1, wherein said antibodies against activated T lymphocytes are selected from antibody against CD69 and integrin ~$\alpha 4\beta 7$ antibody.

3. The column of claim 1, wherein said antibodies against activated neutrophil granulocytes are selected from antibodies against CD66b.

4. The column of claim 1, wherein said antibodies against activated eosinophil granulocytes are selected from antibodies against CD9.

5. An apparatus for leukapheresis comprising the column of claim 1, a blood pump coupled in line with the column, and means for coupling the pump and the column to the venous system of the subject.

6. The apparatus of claim 5, wherein the means of coupling the pump and the column to the venous system of the subject comprise two cannulae.

7. The column of claim 1, wherein the biopsy sample has been mechanically treated to obtain a cell suspension.

8. An apparatus for leukapheresis comprising the column of claim 1, a blood pump coupled in line with the column, wherein the pump is coupled to the venous system of the subject.

9. The apparatus of claim 8, wherein the pump is coupled to the venous system of the subject with two cannulae.

10. A combination of two or more leukapheresis columns of claim 1 coupled in parallel or in line.

11. A method of treating inflammatory bowel disease (IBD) in a subject, comprising:
    providing one or more columns of claim 1;
    diverting a portion of the subject's peripheral blood through the column, thereby eliminating activated leukocytes from the subject's peripheral blood; and
    re-infusing the subject's peripheral blood to the subject, thereby treating IBD in the subject.

12. The method of claim 11, wherein a combination of one or more leukapheresis columns is coupled in parallel or in line.

13. The method of claim 11, wherein the one or more columns comprises a single column.

14. The method of claim 11, wherein from about one third to about two thirds of the subject's blood volume is passed through the column in a single treatment.

15. The method of claim 11, wherein about half of the subject's blood volume is passed through the column in a single treatment.

16. The method of claim 11, wherein the treatment is repeated at least three times over about a one to three week period.

17. The method of claim 11, wherein the one or more columns comprise antibodies against CD69 and integrin ~$\alpha 4\beta$.

18. The method of claim 11, wherein the one or more columns comprise antibodies against CD66b.

19. The method of claim 11, wherein the one or more columns comprise antibodies against CD9.

20. The method of claim 11, wherein the treatment is repeated at least five times over about a one to three week period.

* * * * *